United States Patent [19]

Engelbach et al.

[11] 4,282,374

[45] Aug. 4, 1981

[54] PREPARATION OF GLYOXAL FROM ETHYLENE GLYCOL

[75] Inventors: Heinz Engelbach, Limburgerhof; Michael J. Sprague, Mannheim, both of Fed. Rep. of Germany

[73] Assignee: BASF Aktiengesellschaft, Fed. Rep. of Germany

[21] Appl. No.: 54,871

[22] Filed: Jul. 5, 1979

[30] Foreign Application Priority Data

Jul. 24, 1978 [DE] Fed. Rep. of Germany ....... 2832405

[51] Int. Cl.³ ............................................. C07C 45/65
[52] U.S. Cl. .................................................. 568/471
[58] Field of Search ...................... 260/603 C; 568/471

[56] References Cited

U.S. PATENT DOCUMENTS

| | | | |
|---|---|---|---|
| 2,339,282 | 1/1944 | McNamee et al. | 260/603 C |
| 2,339,346 | 1/1944 | McNamee et al. | 260/603 C |
| 2,339,347 | 1/1944 | McNamee et al. | 260/603 C |
| 2,339,348 | 1/1944 | McNamee et al. | 260/603 C |

FOREIGN PATENT DOCUMENTS

| | | | |
|---|---|---|---|
| 1923048 | 11/1969 | Fed. Rep. of Germany | 260/603 C |
| 2158343 | 5/1972 | Fed. Rep. of Germany | 260/603 C |
| 2158344 | 5/1972 | Fed. Rep. of Germany | 260/603 C |
| 2634439 | 10/1977 | Fed. Rep. of Germany | 260/603 C |
| 199886 | 7/1923 | United Kingdom | 260/603 C |
| 1272592 | 5/1972 | United Kingdom | 260/603 C |

*Primary Examiner*—Werren B. Lone
*Attorney, Agent, or Firm*—Keil & Witherspoon

[57] ABSTRACT

A process for the preparation of glyoxal by vapor phase oxidation of ethylene glycol with oxygen over a copper-containing oxidation catalyst at an elevated temperature and in the presence of a phosphorus compound which is volatile under the reaction conditions, the amount of phosphorus (calculated as P) being from 1 to 100 ppm, based on the weight of ethylene glycol.

4 Claims, No Drawings

PREPARATION OF GLYOXAL FROM ETHYLENE GLYCOL

U.S. Pat. Nos. 2,339,282 and 2,339,346 to 2,339,348 disclose that glyoxal can be prepared from ethylene glycol by vapor phase oxidation in the presence of oxygen over a catalyst based on copper or copper oxide, at from 225° to 450° C. If, in accordance with the disclosures of German Laid-Open Application DOS No. 1,923,048, germanium, tin, lead, nitrogen, phosphorus, arsenic, antimony or bismuth is added to the copper-containing catalysts, glyoxal yields of up to 72% are achieved. According to the process of German Laid-Open Application DOS No. 2,634,439, bromine compounds are added to the gaseous mixture.

A substantial disadvantage of these conventional processes is that the catalyst ages relatively rapidly so that the yield soon decreases. For example, it has been found that the yield of glyoxal, when using copper turnings as the catalyst at 310° C., and carrying out the process continuously, drops from about 68 to about 59% after only 73 hours' operation. If a catalyst described in German Laid-Open Application DOS No. 1,923,048 is employed for the oxidation of ethylene glycol to glyoxal, the catalyst selectivity decreases, according to German Laid-Open Application DOS No. 2,158,343, from an initial value of 60–64% to 55% after 700 hours' operation. German Laid-Open Application DOS No. 2,158,344 discloses that after 18 days' operation the selectivity of a catalyst described in German Laid-Open Application DOS No. 1,923,048 falls to 54% from its initial value of 58%. It has been proposed to regenerate copper-containing catalysts by either an oxidizing or a reducing treatment, entailing interruption of normal operation. According to the disclosures of German Laid-Open Application DOS No. 2,158,343, a Cu-Ag-P catalyst is regenerated, after 700 hours' operation, by reduction at 450° C. for 12 hours. German Laid-Open Application DOS No. 2,158,344 describes the regeneration of a Cu-P catalyst, after 18 days' operation, by passing an excess of oxygen over the catalyst for at least 1 day.

These regeneration processes have the disadvantage that they entail a production stoppage and require expensive safety measures in order to ensure that the air used for regeneration does not mix with the reaction gas.

We have found that in the preparation of glyoxal by vapor phase oxidation of ethylene glycol with an oxygen-containing gas in the presence of a copper-containing oxidation catalyst at an elevated temperature, the life of the catalyst can be substantially increased if the vapor phase oxidation is carried out in the presence of a phosphorus compound which is volatile under the reaction conditions, the amount of phosphorus (calculated as P) being from 1 to 100 ppm, based on the weight of ethylene glycol.

Surprisingly, phosphorus only exhibits this advantageous effect when it is in the form of compounds which are volatile under the reaction conditions, in which case even very small amounts of P suffice. Preferably, the amount of phosphorus (calculated as P) is from 2 to 25 ppm, based on the weight of ethylene glycol. Advantageously, phosphorus compounds which have a boiling point close to that of ethylene glycol are used. Examples of suitable phosphorus compounds are trimethyl phosphate, triethyl phosphate, tri-iso-propyl phosphate, tri-n-propyl phosphate, trimethyl phosphite, triethyl phosphite, triethylphosphine oxide, diethyl methylphosphonate, dimethyl methylphosphonate and diethyl ethylphosphonate.

The vapor phase oxidation of ethylene glycol with the oxygen-containing gas over the copper-containing catalyst is carried out in the conventional manner, for example at from about 225° to about 500° C. Examples of suitable copper-containing catalysts are metallic copper, copper-containing alloys or compounds with metals or non-metals, eg. copper phosphides, copper bronzes or alloys of copper with silver and/or gold, copper ores, eg. malachite and copper compounds which can be completely or partially reduced to copper during the reaction, eg. copper(I) oxide, copper(II) oxide and compounds which on heating are converted to copper oxides, eg. copper nitrate and copper acetate. Copper phosphate and copper antimonate are also suitable. Additionally, other metal oxides or non-metal oxides, eg. zinc, chromium, phosphorus, antimony, tin and bismuth oxides, may be mixed with the copper-containing compounds. The copper-containing catalytic material can also be applied to an inert carrier or be diluted with an inert material. If desired, the catalyst can also be subjected to a reducing treatment before use.

Copper-containing catalysts which do not have a large inner surface, for example those with a surface of less than 50 m$^2$/g, are preferred. Metallic copper, and alloys which contain copper as a substantial constituent, are of particular industrial interest. They are used, for example, in the form of turnings, wire fabrics or gauzes, or as supported catalysts on an inert carrier, for example a carrier of low surface area.

The process is carried out, for example, by passing a gaseous mixture of ethylene glycol and water (containing from 0.1 to 99% of water) together with from about 0.5 to 2.0 moles of oxygen, per mole of ethylene glycol employed, and with or without nitrogen (in an amount of from 0 to 99% by volume of the total gaseous mixture) over the catalyst which is kept at 225°–500° C., the volatile phosphorus compound being added beforehand to the gaseous starting mixture. The gaseous product mixture leaving the reactor is scrubbed with water in the conventional manner.

EXAMPLE 1

25.25 parts of copper turnings are introduced into a V2A steel tubular reactor, having an inner diameter of 21 mm, to give a catalyst bed height of 18 cm. Per hour, a gaseous mixture of 6.38 parts by weight of ethylene glycol, 2.04 parts by weight of water, 0.00019 part by weight of trimethyl phosphate (CH$_3$O)$_3$PO (representing 6.58 ppm of P, based on the weight of ethylene glycol), 3,465 parts by volume of oxygen and 188,000 parts by volume of nitrogen is passed continuously over the catalyst, which is kept at 300° C. The product mixture is washed out of the gas stream, leaving the reactor, by means of water. Analysis of the aqueous solution obtained gives the following result:

Amount of ethylene glycol employed = 421.0 parts by weight

Aqueous product solution = 1818.5 parts by weight

According to titrimetric determination, the product solution contains:

14.5% by weight of glyoxal = 263.7 parts (corresponding to a yield of glyoxal, based on ethylene glycol employed, of 67.0% of theory).

After a further uninterrupted period of operation of 96 hours, the following results are obtained:
Amount of ethylene glycol employed = 45.32 parts
Aqueous product solution = 537.99 parts
The product solution contains:
4.74% by weight of glyoxal = 25.50 parts
(corresponding to a yield of glyoxal, based on ethylene glycol employed, of 60.2% of theory).

COMPARATIVE EXAMPLE (no added volatile P compound)

The procedure described in Example 1 is followed, but in this case a gaseous mixture of 6.56 parts by weight of ethylene glycol, 2.10 parts by weight of water, 3,570 parts by volume of oxygen and 188,000 parts by volume of nitrogen is passed, per hour, over the catalyst kept at 310° C.

The following result is obtained:
Amount of ethylene glycol employed = 32.01 parts by weight
Aqueous product solution = 360.42 parts by weight
The product solution contains:
5.61% by weight of glyoxal = 20.22 parts
(corresponding to a yield of glyoxal, based on ethylene glycol employed, of 67.6% of theory).

After a further uninterrupted period of operation of 73 hours, the following results are obtained:
Amount of ethylene glycol employed = 40.41 parts
Aqueous product solution = 451.72 parts
The product solution contains:
4.90% by weight of glyoxal = 22.13 parts
(corresponding to a yield of glyoxal, based on ethylene glycol employed, of 58.6% of theory)

EXAMPLE 2

In a tubular reactor, charged with copper turnings as described in Example 1, a gaseous mixture of 6.53 parts of ethylene glycol, 2.08 parts of water, 0.000389 part of trimethyl phosphate $(CH_3O)_3PO$ (representing 13.2 ppm of P, based on the weight of ethylene glycol), 3,465 parts by volume of oxygen and 188,000 parts by volume of nitrogen is passed continuously, per hour, over the catalyst which is kept at 310° C. The gas stream leaving the reactor is worked up as described in Example 1. The following result is obtained:
Amount of ethylene glycol employed = 38.84 parts
Aqueous product solution = 560.33 parts
The product solution contains
4.40% by weight of glyoxal = 24.65 parts
(corresponding to a yield of glyoxal, based on ethylene glycol employed, of 67.9% of theory).

After a further uninterrupted period of operation of 1,166 hours, the following result is obtained:
Amount of ethylene glycol employed = 37.43 parts
Aqueous product solution = 508.86 parts The product solution contains
4.46% by weight of glyoxal = 22.70 parts
(corresponding to a yield of glyoxal, based on ethylene glycol employed, of 64.8% of theory).

COMPARATIVE EXAMPLE (too much volatile P compound)

In a tubular reactor, charged with copper turnings as described in Example 1, a gaseous mixture of 6.19 parts of ethylene glycol, 1.97 parts of water, 0.00367 part of trimethyl phosphate $(CH_3O)_3PO$ (representing 131 ppm of P, based on the weight of ethylene glycol), 2,645 parts by volume of oxygen and 185,000 parts by volume of nitrogen is passed continuously, per hour, over the catalyst which is kept at 300° C. The gas stream leaving the reactor is worked up as described in Example 1. The following result is obtained:
Amount of ethylene glycol employed = 37.63 parts
Aqueous product solution = 461.64 parts
The product solution contains:
5.20% by weight of glyoxal = 24.01 parts
(corresponding to a yield of glyoxal, based on ethylene glycol employed, of 68.2% of theory).

After a further uninterrupted period of operation of 48 hours, the following result is obtained:
Amount of ethylene glycol employed = 37.02 parts by weight
Aqueous product solution = 543.71 parts by weight
The product solution contains:
3.49% by weight of glyoxal = 18.98 parts
(corresponding to a yield of glyoxal, based on ethylene glycol employed, of 53.9% of theory).

COMPARATIVE EXAMPLE (P alone used in the catalyst)

A mixture of copper powder and antimony phosphate $(SbPO_4)$ is applied, by flame spraying, to steatite beads which have a diameter of 6 mm and a rough surface. The resulting catalyst contains about 161 g of active material, comprising 88.6 percent by weight of Cu, 0.5 percent by weight of Sb and 0.097 percent by weight of P, per liter of carrier. 63.03 parts of this catalyst are introduced into a V2A steel tubular reactor of 21 mm internal diameter. A gaseous mixture of 6.75 parts of ethylene glycol, 2.16 parts of water, 2,940 parts by volume of oxygen and 186,000 parts by volume of nitrogen is passed continuously, per hour, over the catalyst which is kept at 325° C. The product mixture is washed out of the gas stream, leaving the reactor, with water, and the resulting aqueous solution is analyzed.

The following result is obtained:
Amount of ethylene glycol employed = 122.31 parts
Aqueous product solution = 969.64 parts
The product solution contains:
7.89% by weight of glyoxal = 76.50 parts
(corresponding to a yield of glyoxal, based on ethylene glycol employed, of 66.9% of theory).

After a further uninterrupted period of operation of 48 hours, the following results are obtained:
Amount of ethylene glycol employed = 124.52 parts
Aqueous product solution = 965.78 parts
The product solution contains:
7.01% by weight of glyoxal = 67.70 parts
(corresponding to a yield of glyoxal, based on ethylene glycol employed, of 58.1% of theory).

EXAMPLE 3

A catalyst is produced by flame spraying similarly to the preceding Comparative Example. This catalyst contains about 179 g of active material, comprising 90.2 percent by weight of Cu, 0.8 percent by weight of Sb and 0.08 percent by weight of P, per liter of steatite carrier. 65.92 parts of the catalyst are introduced into a V2A steel tubular reactor of 21 mm internal diameter. A gaseous mixture of 6.58 parts of ethylene glycol, 2.10 parts of water, 0.000196 part of trimethyl phosphate $(CH_3O)_3PO$ (representing 6.59 ppm of P, based on the weight of ethylene glycol), 3,570 parts by volume of oxygen and 188,500 parts by volume of nitrogen is then passed continuously, per hour, over the catalyst which is kept at 335° C. The product mixture is washed out of the gas stream, leaving the ractor, with water, and the resulting aqueous solution is analyzed.

The following results are obtained:
Amount of ethylene glycol employed = 118.16 parts
Aqueous product solution = 438.71 parts
The product solution contains:
  17.44% by weight of glyoxal = 76.69 parts
(corresponding to a yield of glyoxal, based on ethylene glycol employed, of 69.4% of theory)

After a further almost uninterrupted period of operation of 2,654 hours, the following results are obtained:
Amount of ethylene glycol employed = 37.20 parts
Aqueous product solution = 519.97 parts
The product solution contains:
  4.46% by weight of glyoxal = 23.19 parts
(corresponding to a yield of glyoxal, based on ethylene glycol employed, of 66.7% of theory)

EXAMPLE 4

63.07 parts of the catalyst described in Example 3 are introduced into a V2A steel tubular reactor of 21 mm internal diameter. A gaseous mixture of 6.65 parts of ethylene glycol, 2.12 parts of water, 0.000396 part of trimethyl phosphate $(CH_3O)_3PO$ (representing 13.2 ppm of P, based on the weight of ethylene glycol), 3,250 parts by volume of oxygen and 187,000 parts by volume of nitrogen is then passed continuously, per hour, over the catalyst kept at 335° C. The product mixture is washed out of the gas stream, leaving the reactor, with water, and the resulting aqueous solution is analyzed.

The following result is obtained:
Amount of ethylene glycol employed = 40.39 parts
Aqueous product solution = 426.65 parts
The product solution contains:
  5.95% by weight of glyoxal = 25.39 parts
(corresponding to a yield of glyoxal, based on ethylene glycol employed, of 67.2% of theory)

After a further uninterrupted period of operation of 428 hours, the following result is obtained:
Amount of ethylene glycol employed = 39.61 parts
Aqueous product solution = 420.32 parts
The product solution contains:
  5.44% by weight of glyoxal = 22.87 parts
(corresponding to a yield of glyoxal, based on ethylene glycol employed, of 61.7% of theory)

EXAMPLE 5

65.66 parts of the catalyst described in Example 3 are introduced into a V2A steel tubular reactor of 21 mm internal diameter. A gaseous mixture of 6.47 parts of ethylene glycol, 2.06 parts of water, 0.000771 part of trimethyl phosphate $(CH_3O)_3PO$ (representing 26.3 ppm of P, based on the weight of ethylene glycol), 3,250 parts by volume of oxygen and 187,000 parts by volume of nitrogen is then passed continuously, per hour, over the catalyst kept at 335° C. The product mixture is washed out of the gas stream, leaving the reactor, with water, and the resulting aqueous solution is analyzed.

The following result is obtained:
Amount of ethylene glycol employed = 39.39 parts
Aqueous product solution = 398.7 parts
The product solution contains:
  6.13% by weight of glyoxal = 24.44 parts
(corresponding to a yield of glyoxal, based on ethylene glycol employed, of 66.4% of theory)

After a further uninterrupted period of operation of 221 hours, the following result is obtained:
Amount of ethylene glycol employed = 40.67 parts
Aqueous product solution = 409.41 parts
The product solution contains:
  5.52% by weight of glyoxal = 22.60 parts
(corresponding to a yield of glyoxal, based on ethylene glycol employed, of 59.4% of theory)

EXAMPLE 6

64.7 parts of the catalyst described in Example 3 are introduced into a V2A steel tubular reactor of 21 mm internal diameter. A gaseous mixture of 6.90 parts of ethylene glycol, 2.20 parts of water, 0.00206 part of trimethyl phosphate $(CH_3O)_3PO$ (representing 66 ppm of P, based on the weight of ethylene glycol), 3,250 parts by volume of oxygen and 177,000 parts by volume of nitrogen is passed continuously, per hour, over the catalyst kept at 335° C. The product mixture is washed out of the gas stream, leaving the reactor, with water, and the resulting aqueous solution is analyzed.

The following result is obtained:
Amount of ethylene glycol employed = 41.37 parts
Aqueous product solution = 487.07 parts
The product solution contains:
  5.28% by weight of glyoxal = 25.72 parts
(corresponding to a yield of glyoxal, based on ethylene glycol employed, of 66.5% of theory)

After a further uninterrupted period of operation of 48 hours, the following result is obtained:
Amount of ethylene glycol employed = 124.87 parts
Aqueous product solution = 1110.88 parts
The product solution contains:
  6.34% by weight of glyoxal = 70.34 parts
(corresponding to a yield of glyoxal, based on ethylene glycol employed, of 60.3% of theory).

We claim:

1. A process for the preparation of glyoxal by vapor phase oxidation of ethylene glycol with an oxygen-containing gas in the presence of a copper-containing oxidation catalyst at a temperature of from about 225° to about 500° C., wherein the vapor phase oxidation is carried out in the presence of a phosphorus compound having a boiling point of less than about 500° C. under the reaction conditions, the amount of phosphorus (calculated as P) being from 1 to 100 ppm, based on the weight of ethylene glycol.

2. The process of claim 1, wherein the phosphorus compound which is volatile under the reaction conditions is added to the ethylene glycol to be fed to the vapor phase oxidation.

3. The process of claim 1, wherein the amount of phosphorus (calculated as P) is from 2 to 25 ppm, based on the weight of ethylene glycol.

4. The process of claim 1, wherein trimethyl phosphate, triethyl phosphate, tri-isopropyl phosphate, tri-n-propyl phosphate, trimethyl phosphite, triethyl phosphite, triethylphosphine oxide, diethyl methylphosphonate, dimethyl methylphosphonate or diethyl ethylphosphonate is used as the phosphorus compound which is volatile under the reaction conditions.

* * * * *